(12) United States Patent
Davis et al.

(10) Patent No.: US 6,224,578 B1
(45) Date of Patent: May 1, 2001

(54) DRIP CHAMBER ANTI FREE FLOW DEVICE

(75) Inventors: Mark A. Davis, St. Paul, MO (US); Glen G. Fournie, Smithton, IL (US); John P. Moran, Herculaneum, MO (US); Clarence L. Walker, St. Louis; Angela M. Noecker, Richmond Heights, both of MO (US)

(73) Assignee: Sherwood Services, AG (CH)

( * ) Notice: Subject to any disclaimer, the term of this patent is extended or adjusted under 35 U.S.C. 154(b) by 0 days.

(21) Appl. No.: 09/564,266

(22) Filed: May 4, 2000

(51) Int. Cl.[7] .................................................. A61M 5/00
(52) U.S. Cl. ............................................. 604/247; 604/30
(58) Field of Search ................................ 604/247, 30, 31, 604/32, 33, 245, 34, 246, 251, 254, 255, 256; 137/409

(56) References Cited

U.S. PATENT DOCUMENTS

| | | | |
|---|---|---|---|
| 3,311,268 | 3/1967 | Fields | 222/159 |
| 3,460,529 | 8/1969 | Leucci | 128/2 |
| 3,547,401 | 12/1970 | Beall et al. | 251/144 |
| 4,263,932 | 4/1981 | Laar et al. | 137/101.27 |
| 4,395,260 | 7/1983 | Todd et al. | 604/122 |
| 4,615,693 | 10/1986 | Paradis et al. | 64/122 |
| 4,850,393 | 7/1989 | Lashomb | 137/528 |
| 5,019,055 | 5/1991 | O'Boyle | 604/249 |
| 5,267,586 | 12/1993 | Jankavaara | 137/565 |
| 5,868,715 | 2/1999 | Tung | 604/256 |

*Primary Examiner*—Manuel Mendez
(74) *Attorney, Agent, or Firm*—Greensfelder, Hemker & Gale, P.C.

(57) ABSTRACT

A valve device is disclosed which is incorporated into the lower portion of a drip chamber for preventing the free flow of fluid through a tube assembly when the tube assembly is disengaged from a pump of a fluid administration system, while permitting fluid flow when the tube assembly is engaged around a rotor of the pump. The valve device comprises a valve body having a top component sealingly engaged with a bottom component. The top component is integrally formed with the lower portion of the drip chamber and defines a plurality of axial fluid passageways formed around a stationary plunger which seals against a opening formed at the upper portion of the bottom component. The opening is in communication with a lumen that extends into a hollow tube assembly which is attached to the bottom component of the valve body. The bottom component further includes a flex joint made of a flexible material that is adapted to flex and pull the opening away from the plunger to establish fluid flow through the valve device. In operation, a user applies a tensile force along the tube assembly by engaging the tube assembly around a rotor of a pump which pulls the flex joint away from the plunger and opens the valve device to fluid flow therethrough. When the tube assembly is disengaged from the rotor the flex joint is forced back to its original position such that the plunger is sealed against the opening, thereby preventing fluid free flow through the fluid administration system.

23 Claims, 4 Drawing Sheets

DRIP CHAMBER ANTI FREE FLOW DEVICE

BACKGROUND OF THE INVENTION

1. Field of the Invention

The present invention relates to a device for preventing fluid free flow through a tube assembly of a fluid administration system, and more particularly to an anti-free flow valve device which is incorporated into a drip chamber of the fluid administration system. More specifically, the present invention relates to an anti-free flow device that prevents fluid free flow when the tube assembly is disengaged from a pump, while allowing fluid flow when the tube assembly is engaged with the pump.

2. Prior Art

Administering fluid, such as medication, saline and nutritional formula, to a patient is well known in the art. Typically, fluid is supplied to a patient by a tube assembly of a fluid administration system which provides a fluid pathway between a fluid source and a patient. The fluid is supplied to the patient through the tube assembly by either an enteral connection which accesses a visceral organ (gastrointestinal feeding) of a patient or through a parenteral connection which accesses a non-visceral organ (intravenous feeding).

Fluid flow rate through the tube assembly may be manually controlled by a mechanical clip which is designed to progressively occlude the tube assembly and selectively impede fluid flow induced by gravity. One such mechanical clip which operates to occlude a portion of the tube assembly is a conventional roller clamp that has a hollow body with opposed openings and a pair of angled slots formed opposite of one another transverse to the openings. The clip further includes a wheel having an axle which is coupled to the body through the slots. A portion of the tube assembly is then inserted through both the openings of the roller clamp and the wheel axially advanced along the slots to pinch a portion of the tube assembly against the body which progressively occludes the tube assembly. Although the mechanical clip operates to provide a cost efficient method for controlling fluid flow rate, the clip must be manually actuated by the user. Further, the wheel of the mechanical clip can be inadvertently bumped or jostled out of position resulting in an inappropriate flow rate.

In order to better enhance fluid flow rate control in a fluid administration system, calibrated pumps have been utilized. One such calibrated pump is a peristaltic pump connected in-line along a portion of the tube assembly between the fluid source and the patient. The peristaltic pump advances the fluid through the tube assembly by progressively occluding successive portions of the tube assembly and urging each occluded portion forward by rotating the rotor of the pump. When a peristaltic pump is utilized to control the fluid flow rate, mechanical clips are typically not employed or are disengaged to prevent the clip from interfering with the operation of the pump.

Although peristaltic pumps have substantially advanced the art, further improvements are required. For example, once the tube assembly is disengaged from the rotor of the pump fluid flow rate through the tube assembly becomes unrestrained as fluid is drawn through the tube assembly by the force of gravity. This situation is known as fluid free flow and may present an undesirable or even life-threatening situation if left undetected because of the risk of overfeeding or overmedicating a patient.

In order to overcome the above-noted drawbacks to fluid administration systems utilizing pumps, several devices have been suggested which operate to automatically occlude a portion of the tube assembly and prevent fluid free flow when the tube assembly becomes disengaged from the rotor of the pump while also permitting uninhibited fluid flow when the tube assembly is properly engaged to the pump. For instance, a variety of automatic occluders have been suggested to improve the art such as those disclosed in U.S. Pat. No. 4,689,043 to Bisha entitled "IV Tube Activator" which describes a clamp for use with a peristaltic pump. The clamp includes a V-shaped channel which is spring biased into a closed position where the narrow portion of the V-shaped channel is sized to substantially crimp, or occlude, a portion of the tube assembly and prevent fluid free flow therethrough. The clamp is placed in an open position by a handle which overlays the pump and depresses the springs such that the tube assembly is positioned within the wider portion of the V-shaped channel to permit unrestricted fluid flow through the tube assembly when the pump is operating. When the handle is released, the V-shaped portion will automatically slide into the closed position and prevent fluid free flow by occluding a portion of the tube assembly.

Another automatic occluder is disclosed in U.S. Pat. No. 5,704,582 to Winterer, et al. entitled "Pinched Clipped Occluder for Infusion Sets" which describes a clip that is positioned between a housing and a cover of a pump. The clip has a plunger biased by a spring against the lumen of the tube assembly so that the lumen becomes occluded by the plunger. Fluid flow through the tube assembly may only be established when the plunger is biased away from the lumen of the tube assembly which occurs when the cover is properly coupled with the housing. However, once the cover becomes disengaged from the housing, the plunger is automatically biased into the closed position by the spring to prevent fluid free flow.

Although both of the aforementioned automatic occluders have advanced the art, both devices are mechanically complex and prone to mechanical failure. In addition, the mechanical complexity of these devices also results in occluders which are expensive to manufacture. Accordingly, there is a need in the art for a valve device which forms an integral part of the tube assembly that is capable of preventing fluid free flow when the tube assembly is disengaged from the pump, while also being mechanically uncomplicated, reliable and low cost to manufacture.

OBJECTS AND SUMMARY OF THE INVENTION

Accordingly, the primary object of the present invention is to provide a valve device which prevents fluid free flow in a fluid administration system.

A further object of the present invention is to provide a valve device that prevents fluid free flow whenever any part of the tube assembly is disengaged from the pump, while permitting fluid flow when the tube assembly is properly engaged to the pump.

Another object of the present invention is to provide a valve device which is operable between a closed position which prevents fluid free flow and an open position which permits fluid flow.

Yet another object of the present invention is to provide a valve device having a flexible joint section that places the valve device in the open and closed positions depending upon whether a tensile force is being applied thereto.

Another further object of the present invention is to provide a valve device that forms an integral part of the drip chamber.

Yet a further object of the present invention is to provide a valve device which permits fluid flow when the tube assembly is in a stretched condition and prevent fluid flow when the tube assembly is in the relaxed condition.

These and other objects of the present invention are realized in the preferred embodiment of the present invention, described by way of example and not by way of limitation, which provides for a valve device for preventing fluid free flow through a tube assembly comprising a drip chamber defining a top component at the lower portion of the drip chamber, the top component having at least one passage formed therethrough and a sealing member. A bottom component is engaged with the top component with the bottom component defining an opening interposed between a chamber and a lumen formed inside the bottom component. The opening is sealingly engageable with the sealing member when the valve device is in the closed position and fluid flow is prevented through the tube assembly. The bottom component further includes a flexible joint that forms a part of a shoulder which is attached to the tube assembly. When the valve device is in a closed position and the tube assembly is in a relaxed condition, the sealing member is sealingly engaged against the opening to prevent fluid flow through the opening. However, when the valve device is in an open position and a tensile force is applied to the tube assembly, the flexible joint stretches and is pulled away relative to the top component such that the opening disengages from the sealing member and permits fluid flow through the opening.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
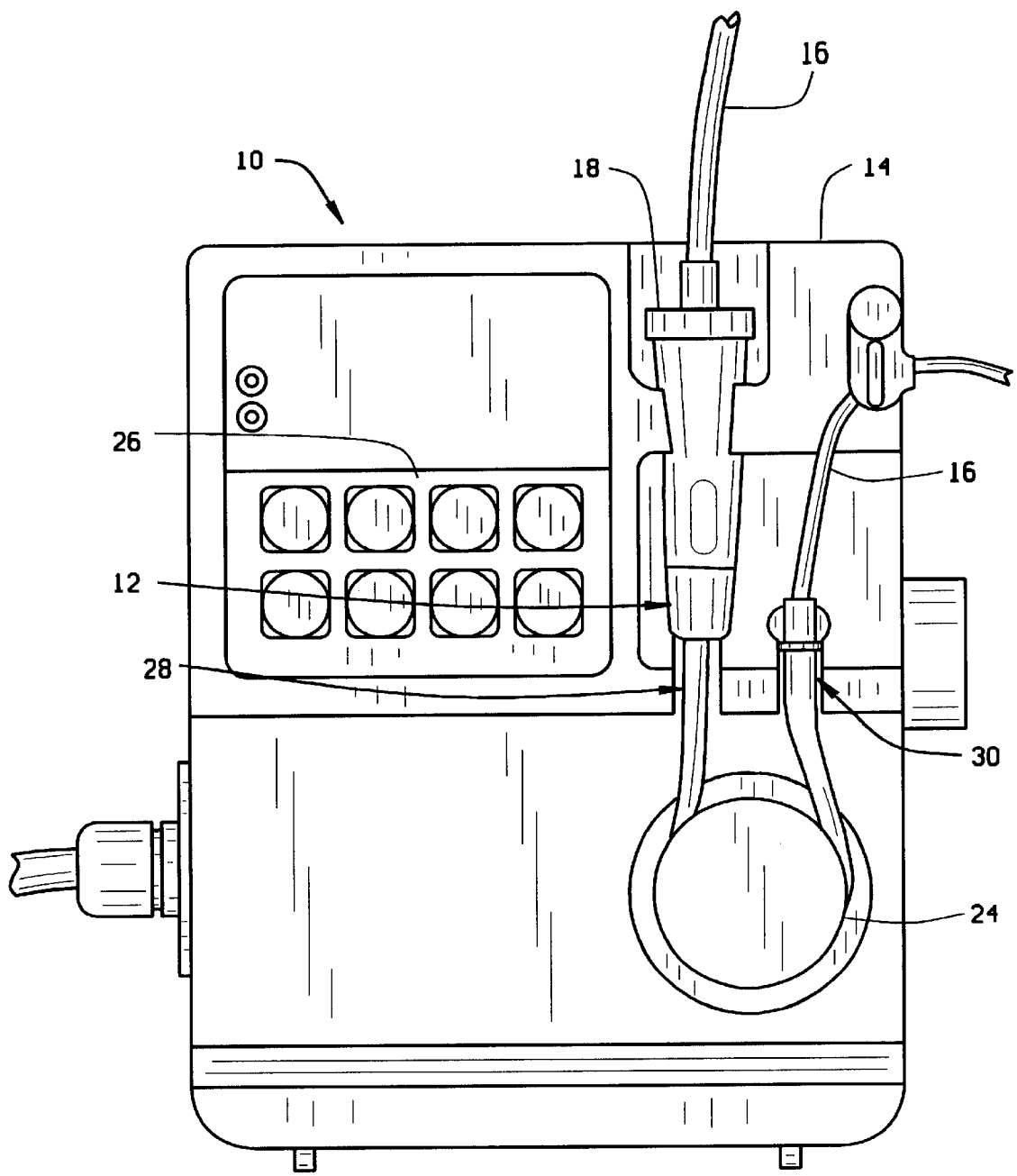
FIG. 1 is a partial front view of the tube assembly engaged with the pump of a fluid administration system according to the present invention.

Referring to the drawings, the preferred embodiment of the anti free flow valve device of the present invention is illustrated and generally indicated as 12 in FIG. 1. The valve device 12 is used in a fluid administration system 10 having a tube assembly 16 and a pump 14 with device 12 incorporated into a drip chamber 18 for preventing fluid free flow when tube assembly 16 is disengaged from pump 14. For ease of reference, proximal shall refer to the end of valve device 12 or tube assembly 16 closest to fluid source 32 while distal shall refer to the end of valve device 12 or tube assembly 16 farthest from fluid source 32 shown in FIG. 2.

Figure 6:
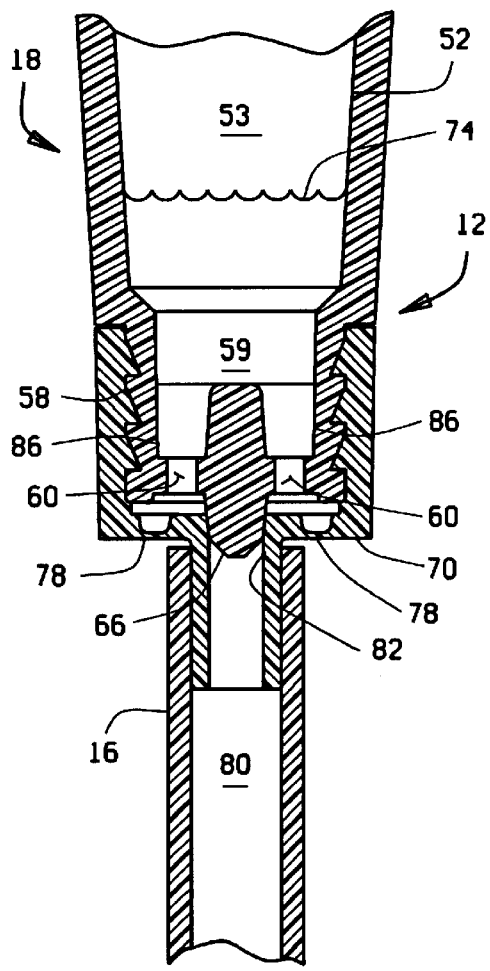
FIG. 6 is a cross sectional view of the valve device taken along line 6—6 of FIG. 2 showing the device in the closed position according to the present invention.

As illustrated in FIGS. 1 and 6, pump 14 is preferably a rotary peristaltic pump, although one skilled in the art can best appreciate that a variety of other pumps, such as linear peristaltic pumps, may be utilized with valve device 12 without departing from the novel aspects of the present invention. Specifically, pump 14 comprises a rotor 24 for advancing fluid 74 through the lumen 80 of the tube assembly 16 and a control panel 26 located adjacent rotor 24 which permits a user to monitor and adjust the rotation rate of rotor 24 for controlling the fluid flow rate of pump 14. Pump 14 further comprises a first recess 28 and a second recess 30 formed into the housing of pump 14 above rotor 24 for engaging and retaining portions of tube assembly 16 in a stretched condition as will be discussed in greater detail below.

Figure 2:
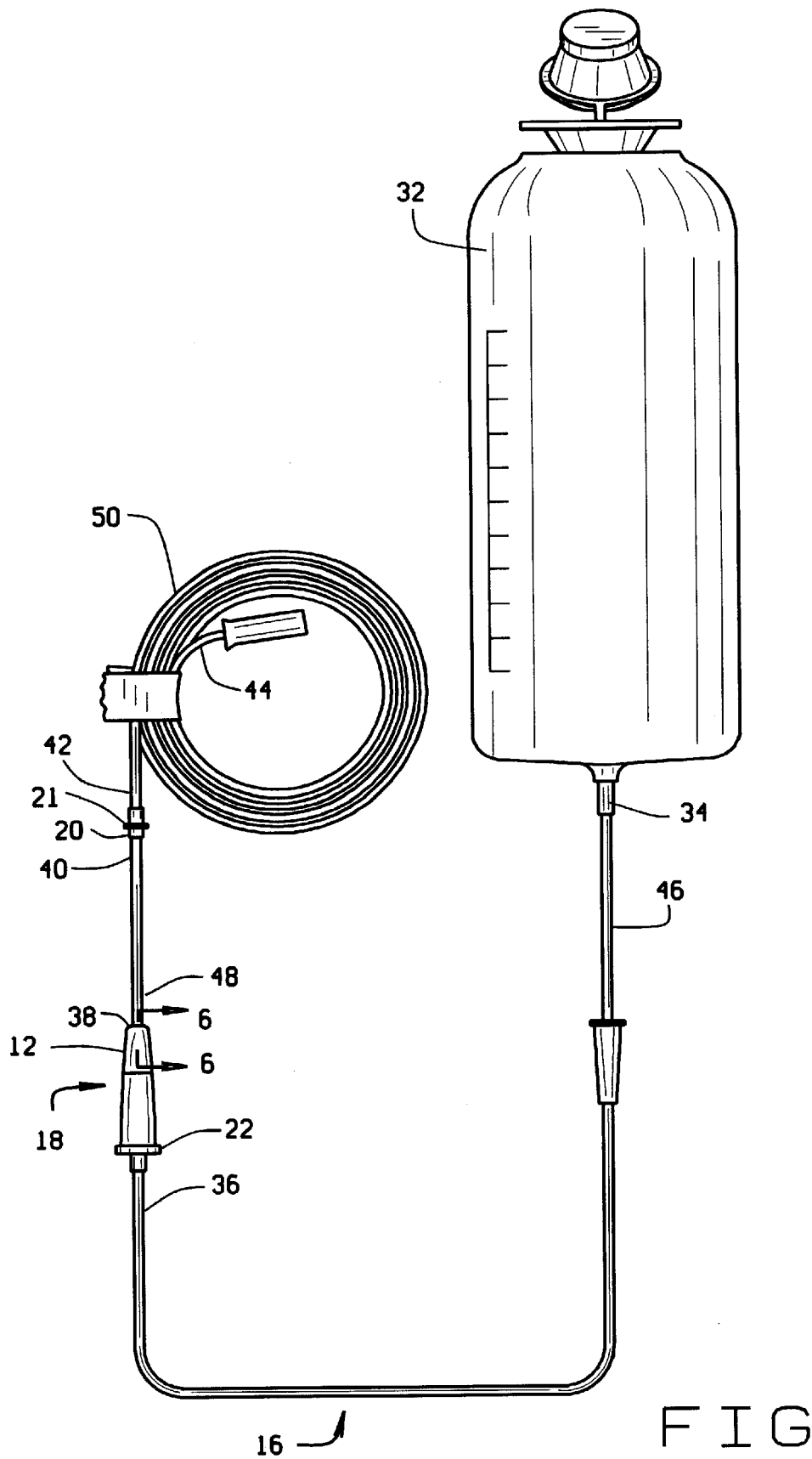
FIG. 2 is a perspective view of the fluid administration system comprising a fluid source and tube assembly having a valve device incorporated into the drip chamber according to the present invention.

Referring to FIG. 2, tube assembly 16 comprises a first tube segment 46, second tube segment 48 and third tube segment 50 which are in communication with one another through a lumen 80 with each tube segment 46, 48 and 50 having a respective proximal end 34, 38 and 42 and a respective distal end 36, 40 and 44. Proximal end 34 of first tube segment 46 is connected to fluid source 32 for providing fluid to a patient, while distal end 36 of tube segment 46 is connected to an abutment surface 22 of drip chamber 18. As discussed briefly above, valve device 12 of the present invention is incorporated into drip chamber 18 and operates to prevent fluid free flow through fluid administration system 10 whenever a tensile force applied to tube assembly 16 is released or tube assembly 16 is disengaged from pump 14. Drip chamber 18 is a metering system for administering measured amounts of fluid 74 to a patient while also interconnecting distal end 36 of first tube segment 46 with the proximal end 38 of second tube segment 48. As further shown, distal end 40 of second tube segment 48 is connected to a coupling 20 having an external flange 21 which interconnects distal end 40 with proximal end 42 of third tube segment 50. Finally, distal end 44 of third tube segment 50 communicates with either an enteral or parenteral connection made with a patient for delivery of fluid 74 through tube assembly 16.

Figure 3:
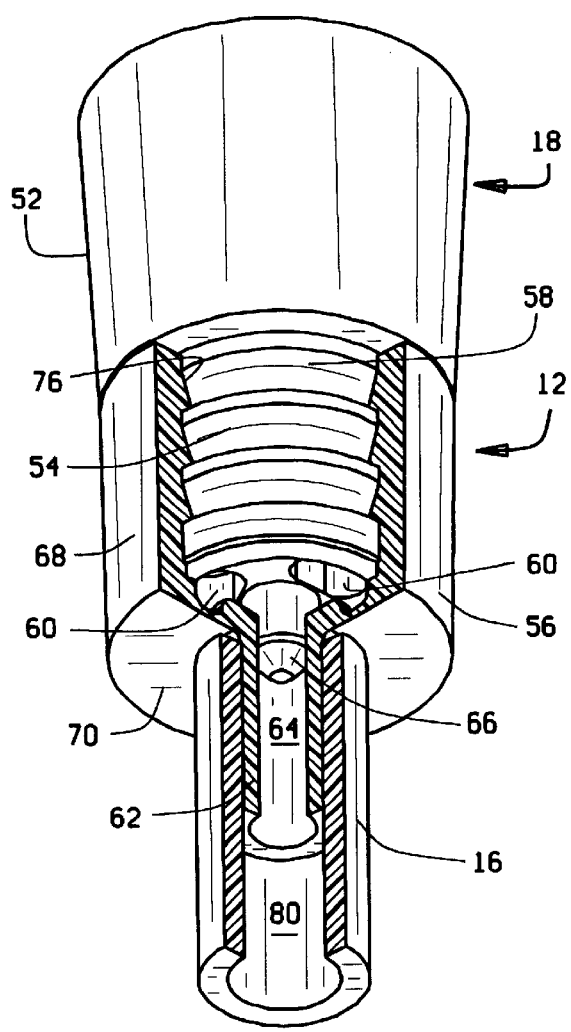
FIG. 3 is a perspective view of the valve device with the top and bottom components cutaway according to the present invention.
Figure 4:
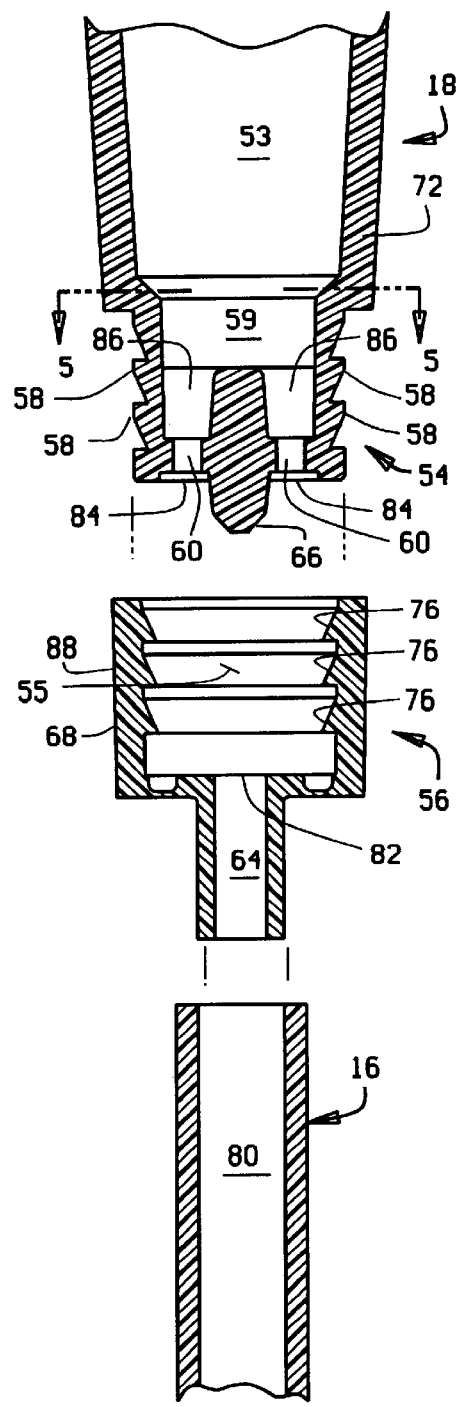
FIG. 4 is an exploded cross sectional view of the valve device according to the present invention.

Referring to FIGS. 3 and 4, the preferred embodiment of valve device 12 is incorporated into drip chamber 18 and includes a top component 54 connected to a bottom component 56. Drip chamber 18 has a wall 72 which defines a primary chamber 53 that stores a measured amount of fluid 74 which enters drip chamber 18 from first tube segment 46. Preferably, top component 54 may be integral with, or in the alternative attached to, drip chamber 18 at its lower portion 52 while bottom component 56 engages top component 54 using a snap fit arrangement between the components. To achieve this snap fit arrangement, top component 54 includes a plurality of annular-shaped barbs 58 which are sized and shaped to engage grooves 76 formed along the interior surface of bottom component 56.

As further shown, a hollow protrusion member 62 extends axially outward from bottom component 56 and defines an inner lumen 64 which communicates with lumen 80 of tube assembly 16 at one end and an opening 82 formed at the other end of inner lumen 64. Bottom component 56 further includes a cylindrical portion 68 having a wall 88 which defines a secondary chamber 55 therein with grooves 76 formed along the interior surface thereof. When top component 54 is properly engaged and aligned with bottom component 56, barbs 58 mate with grooves 76 as illustrated in FIG. 6.

Figure 7:
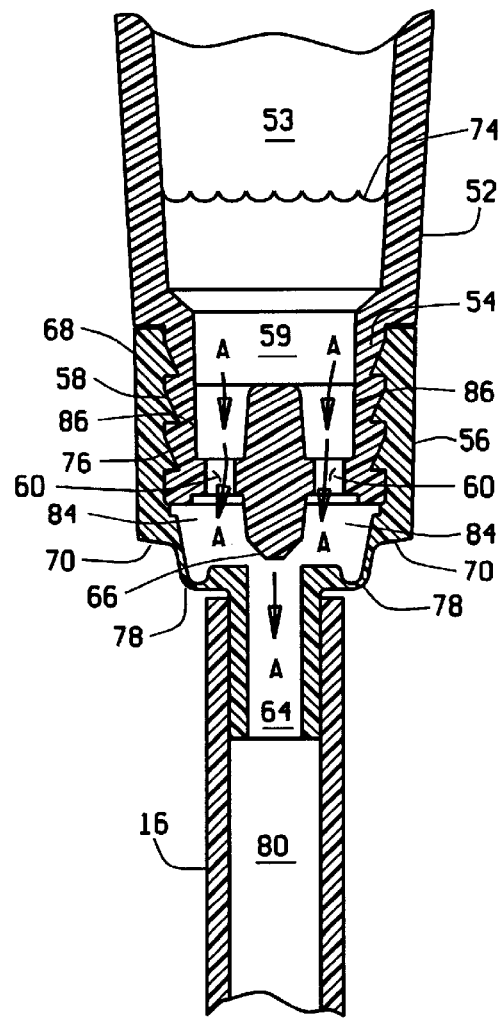
FIG. 7 is a cross sectional view of the valve device taken along line 6—6 of FIG. 2 showing the device in the open position according to the present invention.

One novel aspect of the present invention is the provision of a shoulder 70 which is formed between cylindrical portion 68 and protrusion member 62 of bottom component 56 and provides a means for placing valve device 12 in the open or closed positions. As shown in FIG. 7, shoulder 70 includes an annular flexible joint 78 which surrounds opening 82 and provides sufficient flexibility to shoulder 70 such that flexible joint 78 may be pulled or stretched away relative to the top component 54 when second tube segment 48 is in a stretched condition. Flexible joint 78 has a relatively thinner wall in contrast to the vest of shoulder 70 which has a thicker wall. The flexible joint 78 permits opening 82 to be pulled away from top component 54 when second tube segment 48 is in a stretched condition whenever a tensile force is applied along tube segment 48. The operation of the flexible joint 78 will be explained in greater detail below.

Figure 5:
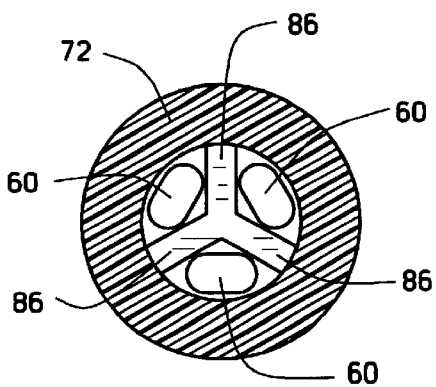
FIG. 5 is a cross sectional view of the valve device taken along line 5—5 of FIG. 4 according to the present invention.

As specifically shown in FIG. 4, top component 54 of valve device 12 defines a primary passage 59 in fluid flow communication with a primary chamber 53 at one end and a plurality of secondary passages 60 separated by ribs 86 (FIG. 5) at the other end thereof. Ribs 86 provide secondary passages 60 with structural reinforcement which prevents deformation and occlusion of passages 60. Each secondary passage 60 communicates with a common reservoir 84 which surrounds a sealing member 66 formed between passages 60 and extends axially outward from top component 54. During manufacturing, top component 54 is engaged with bottom component 56 such that valve device 12 is placed in a closed position whenever tube assembly 16 is in a relaxed condition or free state. In the relaxed condition sealing member 66 is seated in sealing engagement against opening 82 such that fluid flow communication is prevented through secondary passages 60.

Referring to FIGS. 6 and 7, the operation of valve device 12 will be discussed. The user of the present invention first connects the proximal end 34 of first tube segment 46 to fluid source 32 so that fluid flow is initiated through lumen 80 and forces air downstream until fluid 74 reaches drip chamber 18. With the tube assembly in the relaxed condition and disengaged from pump 14, valve device 12 is in the closed position and prevents fluid free flow from drip chamber 18 and into second tube segment 48. In the closed position of valve device 12 shown in FIG. 6, second tube segment 48 is in a relaxed condition such that sealing member 66 is seated against opening 82 in fluid tight engagement thereto. The user may then prime tube assembly 16 in order to evacuate remaining air from the tube assembly 16 by manually applying a tensile force along second tube segment 48. As shown in FIG. 7, applying a tensile force causes shoulder 70 to stretch along the flexible joint 78 such that opening 82 pulls away and becomes unseated from sealing member 66. Once the sealing member 66 becomes unseated from opening 82 fluid flow A is established through secondary passages 60 and through valve device 12 which forces remaining air out through second and third tube segments 48 and 50.

To regulate and urge fluid flow after priming, tube assembly 16 is engaged to pump 14. Specifically, abutment surface 22 of drip chamber 18 is first positioned within first recess 28 by the user and second tube segment 48 is engaged around a portion of rotor 24. External flange 21 of coupling 20 is then inserted into second recess 30 such that a tensile force is applied along second tube segment 48 and places valve device 12 in the open position shown in FIG. 7. As the tensile force is applied along second tube segment 48, it assumes a stretched condition which stretches flexible joint 78 and pulls opening 82 away from its sealing engagement with sealing member 66, thereby permitting fluid flow A through valve device 12. Valve device 12 maintains this open position as long as tube assembly 16 is properly engaged to pump 14. However, if tube assembly 16 becomes disengaged from pump 14 the applied tensile force is released and second tube segment 48 resumes the relaxed condition. Once the tensile force is released, valve device 12 is returned to the closed position shown in FIG. 6 as flexible joint 78 resumes its stationary position and opening 82 becomes reseated against sealing member 66 which prevents fluid free flow.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. A valve device for preventing fluid free flow through a tube assembly comprising:

a drip chamber defining a top component at a lower portion thereof, said top component having at least one passage formed therethrough and a sealing member, and a bottom component engaged with said top component, said bottom component defining an opening interposed between a chamber and a lumen formed inside said bottom component, said opening being sealingly engageable with said sealing member for controlling fluid flow, said bottom component further including a flexible portion attached to the tube assembly for opening and closing the valve device, wherein when the valve device is in the closed position said sealing member is sealingly engaged against said opening to prevent fluid flow through said opening and when said valve device is in the open position said flexible portion is stretched away relative to said top component such that said opening disengages from said sealing member and permits fluid flow through said opening.

2. The valve device according to claim 1, wherein said top component further includes a means for retaining and aligning said top component with said bottom component.

3. The valve device according to claim 2, wherein said means for retaining and aligning comprise a plurality of annular barb members formed around said top component which are engageable with complementary grooves formed inside said bottom component.

4. The valve device according to claim 1, wherein said at least one passage is in fluid communication with a chamber of said drip chamber.

5. The valve device according to claim 1, wherein said at least one passage is in fluid flow communication with said lumen of said bottom component when the valve device is in the open position.

6. The valve device according to claim 5, wherein fluid flow communication between said at least one passage and said lumen is prevented when the valve device is in the closed position.

7. The valve device according to claim 1, wherein a tensile force is applied along said tube assembly when said valve device is placed in the open position.

8. The valve device according to claim 7, wherein said tensile force is released along said tube assembly when the valve device is placed in the closed position.

9. The valve device according to claim 1, wherein said flexible portion is made from a flexible thin elastomeric material.

10. The valve device according to claim 1, wherein said bottom component further includes a protrusion member extending therefrom with said lumen formed through said protrusion member, said lumen being in communication with the tube assembly.

11. The valve device according to claim 1, wherein said flexible portion is more flexible than the rest of said bottom component.

12. An anti free flow system for preventing fluid free flow within a tube assembly comprising:

a drip chamber defining a top component at a lower portion thereof, said top component having at least one passage formed therethrough and a sealing member for sealing off fluid flow, and a bottom component engageable with said top component, said bottom component defining a opening between and in communication with a chamber and a lumen formed inside said bottom component, said opening being sealingly engageable with said sealing member, said bottom member further including a flexible portion attached to the tube assembly for controlling fluid flow through the valve device, wherein when the tube assembly is in a relaxed condition said sealing member is sealingly engaged against said opening to prevent fluid free flow and when the tube assembly is in a stretched condition said opening is disengaged from said sealing member to permit fluid flow.

13. The system according to claim 12, wherein a tensile force is applied along the tube assembly when the tube assembly is in said stretched condition.

14. The system according to claim 13, wherein said tensile force is released along the tube assembly when the tube assembly is in said relaxed condition.

15. The system according to claim 12, wherein said at least one passage, said chamber, and said lumen define a fluid pathway through the valve device when the tube assembly is in a stretched condition.

16. The system according to claim 12, wherein said flexible portion stretches when said tube assembly is in the stretched condition.

17. A valve device for preventing fluid free flow through a tube assembly attached to a pump of a fluid administration system comprising:

a drip chamber defining a primary chamber for holding fluid and a top component formed at a lower portion of said drip chamber, said top component having at least one passage formed therethrough in communication with said primary chamber, said top component further including a sealing member, and a bottom component engaged with said top component, said bottom component defining an opening interposed between a secondary chamber and a lumen formed inside said bottom component, said opening being sealingly engageable with said sealing member for controlling fluid flow, said bottom component further including a flexible portion attached to the tube assembly, wherein when the tube assembly is in a relaxed condition, said flexible portion is stationary such that said sealing member is sealingly engaged against said opening to prevent fluid free flow through the valve device, and when the flexible portion is in the stretched condition said opening is disengaged from said sealing member to permit fluid flow from said primary chamber and through the valve device.

18. A method for preventing fluid free flow in a fluid administration system having a pump which includes a rotor and a tube assembly for the transport of fluid, the method comprising the steps of:

a) providing a valve device having a drip chamber defining a top component at a lower portion thereof, said top component having at least one passage formed therethrough and a sealing member, a bottom component engaged with said top component, said bottom component defining a opening interposed between a chamber and a lumen formed inside said bottom component, said bottom component further including a flexible portion attached to a tube assembly, said sealing element being sealingly engageable against said opening;

b) engaging the tube assembly with the pump;

c) unseating the opening from the sealing member to permit fluid flow through the tube assembly;

d) disengaging the tube assembly from the pump; and e) reseating said opening against said sealing member and preventing fluid free flow through the tube assembly.

19. The method according to claim 18, wherein said step b) further includes applying a tensile force along the tube assembly when engaging the tube assembly around the rotor of the pump.

20. The method according to claim 18, wherein said step d) further includes removing said tensile force along the tube assembly when disengaging the tube assembly from around the rotor of the pump.

21. The method according to claim 18, wherein said step c) further includes stretching said flexible portion such that said opening is disengaged from said sealing member and permit fluid flow through the tube assembly.

22. The method according to claim 18, wherein said step e) further includes placing said flexible portion back to a relaxed condition when reseating said opening against said sealing member and preventing fluid free flow through the tube assembly.

23. The method according to claim 18, wherein said step b) further includes engaging the tube assembly within first and second recesses located on said pump.

* * * * *